(12) United States Patent
Ichihara et al.

(10) Patent No.: US 7,867,708 B2
(45) Date of Patent: Jan. 11, 2011

(54) METHOD OF FORMING SIGNAL PROBE-POLYMER

(75) Inventors: Tatsuo Ichihara, Kawasaki (JP); Mitsugu Usui, Kawasaki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 629 days.

(21) Appl. No.: 11/659,660

(22) PCT Filed: Sep. 8, 2005

(86) PCT No.: PCT/JP2005/016497

§ 371 (c)(1), (2), (4) Date: Feb. 7, 2007

(87) PCT Pub. No.: WO2006/028162

PCT Pub. Date: Mar. 16, 2006

(65) Prior Publication Data

US 2008/0199968 A1 Aug. 21, 2008

(30) Foreign Application Priority Data

Sep. 8, 2004 (JP) ............................. 2004-261543

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ...................... 435/6; 536/23.1, 24.3
See application file for complete search history.

(56) References Cited

U.S. PATENT DOCUMENTS

| | | | |
|---|---|---|---|
| 5,437,977 A * | 8/1995 | Segev | 435/6 |
| 6,261,846 B1 * | 7/2001 | Usui | 436/94 |
| 7,060,814 B2 * | 6/2006 | Usui et al. | 536/24.3 |
| 7,122,310 B2 * | 10/2006 | Usui et al. | 435/6 |
| 7,393,636 B2 * | 7/2008 | Usui et al. | 435/6 |
| 2003/0008294 A1 | 1/2003 | Usui et al. | |
| 2003/0087262 A1 | 5/2003 | Usui et al. | |
| 2004/0009506 A1 | 1/2004 | Stephan et al. | |
| 2006/0286553 A1 | 12/2006 | Usui et al. | |

FOREIGN PATENT DOCUMENTS

| | | |
|---|---|---|
| AU | 4458301 | 3/2002 |
| CA | 2 387 755 | 4/2002 |
| EP | 1 002 877 | 5/2000 |
| EP | 1 188 841 | 3/2002 |
| EP | 1 304 386 | 4/2003 |
| EP | 1 431 386 | 6/2004 |
| JP | 3267576 | 1/2002 |
| JP | 3310662 | 5/2002 |
| JP | 2002-355081 | 12/2002 |
| JP | 2004-187608 | 7/2004 |
| WO | 01/75157 | 10/2001 |
| WO | 02/31192 | 4/2002 |
| WO | 03/040367 | 5/2003 |

OTHER PUBLICATIONS

M.S. Shchepinov et al., "Oligonucleotide Dendrimers: Synthesis and use as Polylabelled DNA Probes", Nucleic Acids Research, vol. 25, No. 22, pp. 4447-4454, 1997.
R. L. Stears et al., "A Novel, Sensitive Detection System for High-Density Microarrays using Dendrimer Technology", Physiol. Genomics, vol. 3, pp. 93-99, 2000.
Supplemental European Search Report dated Nov. 21, 2007.

* cited by examiner

Primary Examiner—Ethan Whisenant
(74) Attorney, Agent, or Firm—Wenderoth, Lind & Ponack, L.L.P.

(57) ABSTRACT

To solve a problem occurring in the PALSAR method that a polymer would be formed in the state of unbound to a captured test gene and thus affect the quantitative characteristics as a nonspecific signal, it is intended to develop a technique whereby the polymer formation is controlled in the step of forming an assembly (polymer) of probes so that the polymer is formed exclusively on a test gene to thereby improve the sensitivity and quantitative characteristics. It is found that the polymer can be quantitatively formed and a nonspecific reaction can be inhibited by, in the step of forming a polymer by reacting plural kinds of probes having abilities to complementarily bind to each other, not adding or reacting these probes at once but starting with the reaction of a first probe in one group, and then reacting the second probe in the other group followed by the reactions of probes one by one (i.e., the first probe, the second probe, and so on).

8 Claims, 8 Drawing Sheets

FIG.2
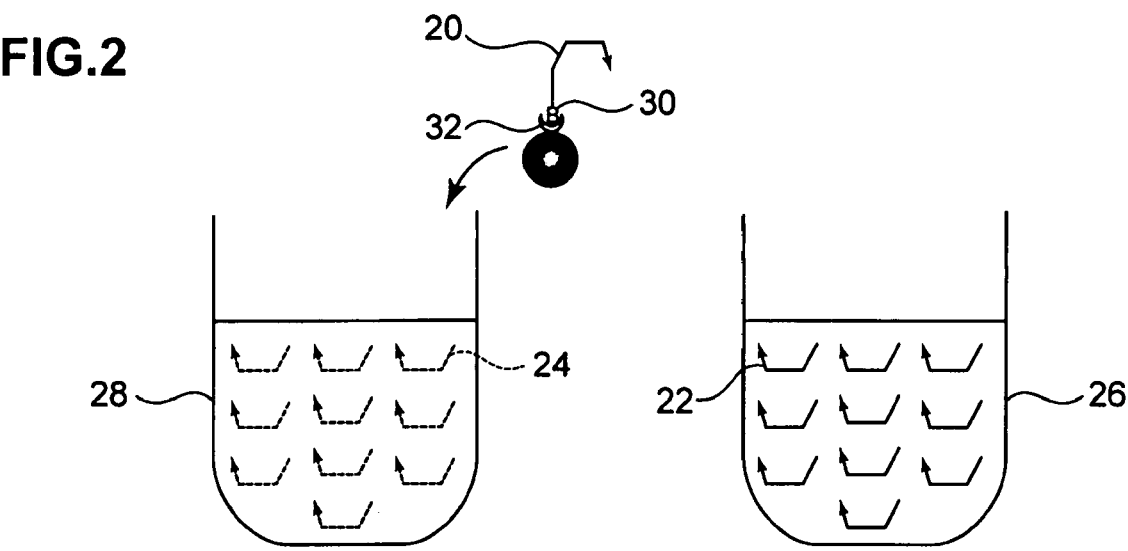
(b)
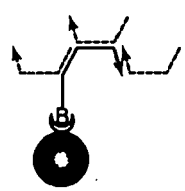
(c)
(d)
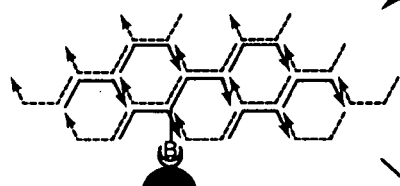
(e)
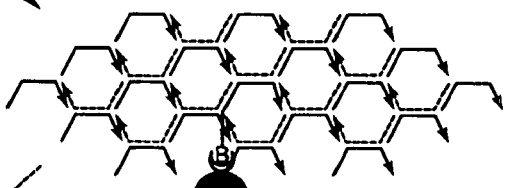
(f)
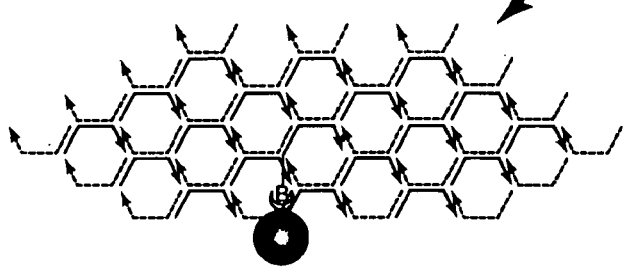

METHOD OF FORMING SIGNAL PROBE-POLYMER

This application is a U.S. national stage of International Application No. PCT/JP2005/016497 filed Sep. 8, 2005.

TECHNICAL FIELD

The present invention relates to: a method of forming an assembly (polymer) of probes by sequentially reacting plural kinds of oligonucleotides that have base sequence regions complementary to each other, in particular, a method of forming a signal probe-polymer that may be used for detection of a test (target) gene in a sample; a polymer formed by the method; and a method of determining the test gene.

BACKGROUND ART

As a method of detecting a small amount of gene in a sample, there is known a polymerase chain reaction method to amplify a gene using enzymes for nucleic acid synthesis, and a number of further improved methods for gene detection have been reported. Meanwhile, there have been reported some methods of detecting a gene by hybridizing oligonucleotides obtained by branching a single-stranded DNA, or the like (Non-Patent Documents 1 and 2).

On the other hand, Usui et al. have reported a novel isothermal nucleic acid amplification method using no enzyme (Patent Documents 1 to 4). This method is intended to form an assembly (polymer) of probes by a self-assembly reaction of plural kinds of oligonucleotides (referred to as probes) that have base sequence regions complementary to each other and is applied to detection of a test gene in a sample by quantification of the polymer. For example, if one of complementary base sequence regions of a probe to be used is designed so as to be a base sequence complementary to a test gene in a sample, this method can detect the test gene effectively by binding the probe to the test gene and then forming a polymer of probes, and it is referred to as PALSAR method.

The PALSAR methods are broadly classified into three groups depending on the kinds of probes to be used. The probes of the first group are two oligonucleotides (referred to as probe-1 and probe-2) which are represented by the following chemical formulas (1) and (2) and which include three complementary base sequence regions, and the regions X and X', Y and Y', and Z and Z' independently have base sequences complementary to each other, so the oligonucleotides can complementarily bind to each other, to thereby form a polymer represented by the following chemical formula (9) (Patent Documents 1 and 2, hereinafter, referred to as PAL-SAR I).

[Chemical Formula 1]

(1)

[Chemical Formula 2]

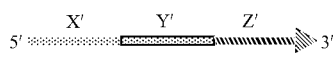
(2)

[Chemical Formula 3]

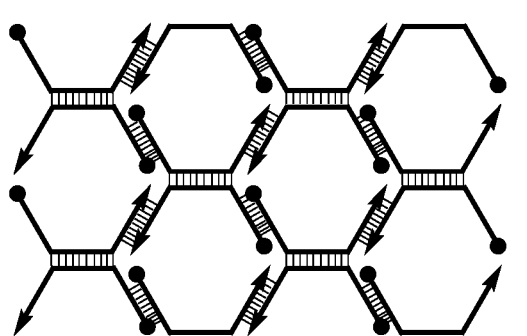
(9)

The probes of the second group are two kinds of probes (referred to as dimer probe-1 and dimer probe-2) which are represented by the following chemical formulas (3) and (4) and have complementary base sequence regions, and if the regions A and A', B and B', C and C', D and D', E and E', and F and F' are designed so as to independently have complementary base sequence regions, the probes can complementarily bind to each other, to thereby form a polymer represented by the chemical formula (9) (Patent Document 3, hereinafter, referred to as PALSAR II).

[Chemical Formula 4]

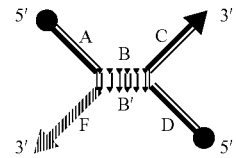
(3)

[Chemical Formula 5]

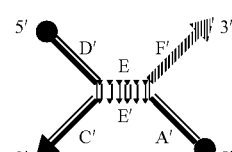
(4)

[Chemical Formula 6]

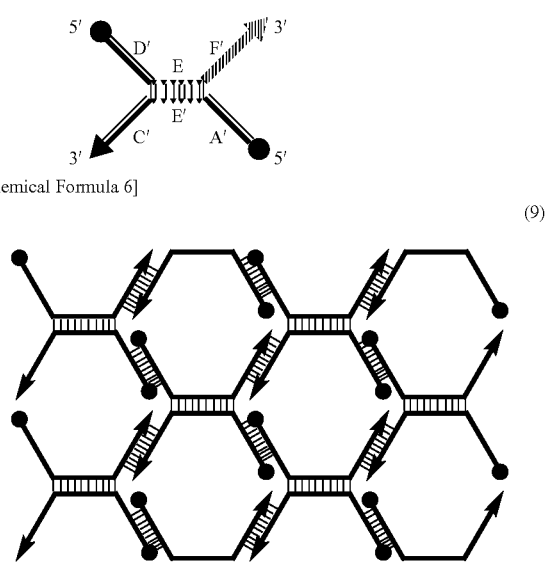
(9)

The probes of the third group are one dimer probe (referred to as dimer probe-3) represented by the following chemical formula (6) and two oligonucleotides (referred to as crosslinking probes) represented by the following chemical formula (7), and if the regions A and A', B and B', C and C', D and D', and F and F' are designed so as to independently have complementary base sequence regions, the dimer probe and the oligonucleotides can complementarily bind to each other, to thereby form a polymer represented by the chemical formula (10) (Patent Document 4, hereinafter, referred to as PALSAR III).

[Chemical Formula 7]

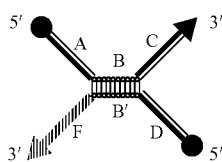

(6)

[Chemical Formula 8]

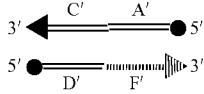

(7)

[Chemical Formula 9]

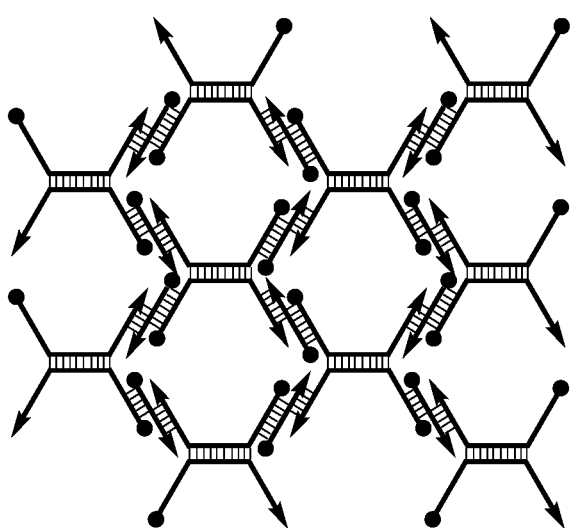

(10)

An example of methods of detecting a test gene in a sample using the PALSAR methods will be described below. For example, in the case of using two kinds of probes, a capture oligonucleotide immobilized to a support is allowed to react with a sample, to thereby capture the gene. In this case, the capture oligonucleotide has a base sequence region complementary to that of the test gene. Subsequently, one probe that has a base sequence region complementary to the base sequence of the gene (other than the part to bind to the capture oligonucleotide) is allowed to react to bind to the gene. Subsequently, both the probes having abilities to complementarily bind to each other are added to form a polymer, and the polymer is quantified to determine the gene.

However, in this unique PALSAR method, if a polymer formation reaction is performed using a reaction solution containing plural kinds of probes having abilities to complementarily bind to each other, the polymer may be formed at a site other than the captured test gene, i.e., in the state of unbound to the test gene, resulting in nonspecific signals that affect quantitative characteristics.

Patent Document 1: Japanese Patent No. 3,267,576
Patent Document 2: International Publication No. WO 01/75157
Patent Document 3: International Publication No. WO 02/31192
Patent Document 4: Published Japanese Application No. 2002-355081
Non-patent Document 1: Shchepinov et. al, Nuc. Acids Res. 1997, 25, 4447-4454
Non-patent Document 2: Stears et. al, Physiol. Genomics, 2000, 3:93-99

DISCLOSURE OF THE INVENTION

Problems to be solved by the Invention

An object of the present invention is to solve the above-described problems accompanied with the PALSAR methods by developing a technique to form a polymer only on a test gene while controlling formation of the polymer in a step of forming an assembly substance (polymer) of probes, to thereby improve sensitivity and quantitative characteristics.

That is, an object of the present invention is to provide a method of forming a signal probe-polymer capable of controlling formation of the polymer and suppressing nonspecific reactions, a polymer formed by the method, and a method of determining a test gene which has excellent detection sensitivity and quantitative characteristics.

Means for Solving the Problems

In view of the above-described problems, the inventors of the present invention have made extensive studies, and as a result they have found out the following. In a step of forming a polymer by reacting plural kinds of probes having abilities to complementarily bind to each other, the polymer can be formed quantitatively while suppressing nonspecific reactions not by adding the probes simultaneously but by reacting the probes one by one in order, that is, the polymer is formed as follows: first, one probe (first probe) is allowed to react, and then the other probe (second probe) is allowed to react, followed by reactions of the first probe and the second probe in order, and the inventors of the present invention thus has accomplished the present invention.

That is, a method of forming a signal probe-polymer of the present invention comprises reacting plural kinds of oligonucleotides (referred to as probes) to form the polymer, wherein the plural kinds of probes have base sequence regions complementary to each other and have abilities to complementarily bind to each other, and the polymer is formed by immobilizing at least one kind of the probes to a test gene and then reacting the plural kinds of probes one by one in order. Note that, a technique of immobilizing the probe to the test gene is not particularly limited, and one of the plural kinds of probes to be used in polymer formation may bind to the test gene directly or indirectly. In the present description, the signal probe-polymer refers to the above-described assembly substance (polymer) formed by the plural kinds of probes.

Preferably, the plural kinds of probes are a probe-1 having a structure of the following chemical formula (1) including three complementary base sequence regions X, Y, and Z and a probe-2 having a structure of the following chemical formula (2) including three complementary base sequence regions X', Y', and Z', and the polymer is formed by reacting the probe-1 and the probe-2 one by one in order.

[Chemical Formula 10]

(1)

[Chemical Formula 11]

(2)

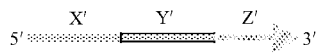

(In the formulas (1) and (2), X and X', Y and Y', and Z and Z' independently have base sequences complementary to each other.)

In addition, preferably, the plural kinds of probes are a dimer probe-1 having a structure of the following chemical formula (3) and a dimer probe-2 having a structure of the following chemical formula (4) or (5), and the polymer is formed by reacting the dimer probe-1 and the dimer probe-2 one by one in order.

[Chemical Formula 12]

(3)

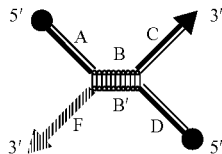

[Chemical Formula 13]

(4)

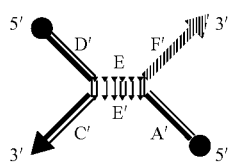

[Chemical Formula 14]

(5)

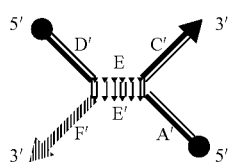

(In the formulas (3) to (5), A and A', B and B', C and C', D and D', E and E', and F and F' independently have base sequences complementary to each other.)

Preferably, the plural kinds of probes are a dimer probe-3 having a structure of the following chemical formula (6) and two crosslinking probes having structures of the following chemical formula (7) or (8), and that the polymer is formed by reacting the dimer probe-3 and the crosslinking probes one by one in order.

[Chemical Formula 15]

(6)

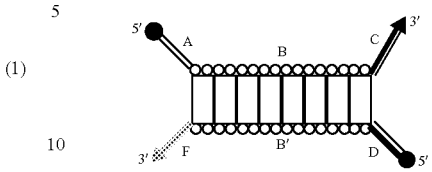

[Chemical Formula 16]

(7)

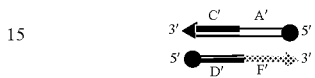

[Chemical Formula 17]

(8)

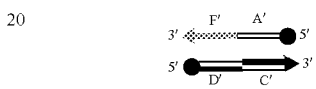

(In the formulas (6) to (8), A and A', B and B', C and C', D and D', and F and F' independently have base sequences complementary to each other.)

In the method of forming a signal probe-polymer of the present invention, preferably, the probes to be used for forming the polymer are labeled with a labeling substance, and more preferably, the labeling substance is a radioactive isotope, biotin, digoxigenin, a fluorescent substance, a luminescent substance, or a dye.

In addition, in the method of forming a signal probe-polymer of the present invention, it is suitable that the polymer is formed by immobilizing an immobilization probe to the test gene and then reacting the plural kinds of probes with the immobilized probe one by one in order, wherein the immobilization probe has the same base sequence as part or a whole of one of the probes to be used for forming the polymer and has a base sequence complementary to the test gene.

Preferably, the plural kinds of probes are the probes-1 and 2, and the immobilization probe has the same base sequence as part or a whole of the probe-1 and has a base sequence complementary to the test gene. Meanwhile, preferably, the plural kinds of probes are the dimer probes-1 and 2, and the immobilization probe has the same base sequence as part or a whole of the dimer probe-1 or 2 and has a base sequence complementary to the test gene. Moreover, preferably, the plural kinds of probes are the dimer probe-3 and the crosslinking probes, and the immobilization probe has the same base sequence as part or a whole of the dimer probe-3 or the crosslinking probes and has a base sequence complementary to the test gene.

The polymer of the present invention is characterized by being formed by the method of forming a signal probe-polymer of the present invention.

The method of determining a test gene of the present invention is characterized by comprising: forming a polymer by the method of forming a signal probe-polymer according to the present invention; and determining the test gene by determining the amount of the formed polymer.

Effect of the Invention

According to the present invention, polymer formation and detection sensitivity can be controlled while suppressing nonspecific reactions by reacting plural kinds of probes having self-assembling abilities one by one in order in a reaction step of forming the polymer using the probes, to thereby improve quantitative characteristics and reproducibility. Moreover, in the reaction step of forming the polymer, a solution containing various probes can be reused.

BRIEF DESCRIPTION OF THE DRAWINGS

FIG. 2 is Illustrative drawings showing an example of a method of forming a signal probe-polymer of the present invention.

DESCRIPTION OF REFERENCE NUMERALS

10: test gene, 12: capture oligonucleotide, 14: immobilization probe, 16: support, 20: immobilized probe, 22: first probe, 24: second probe, 26: first probe reaction tank, 28: second probe reaction tank, 30: biotin, 32: avidin, 40: dimer α, 41: dimer β, 42: dimer formation probe-1, 44: dimer formation probe-2, 46: dimer formation probe-3, 48: dimer formation probe-4, 50: capture oligonucleotide-1, 51: support, 52: immobilization probe-2, 54: immobilization probe-3, 56: test gene, 60: dimer γ, 62: dimer formation probe-5, 64: dimer formation probe-6, 66: crosslinking probe-1, 68: crosslinking probe-2, 70: immobilization probe-3

BEST MODE FOR CARRYING OUT THE INVENTION

Hereinafter, embodiments of the present invention will be described, but it will be obvious that various changes may be made without departing from the scope of the present invention. Hereinafter, the following methods will be sequentially described: (1) a method of immobilizing a probe to a test gene; (2) a method of forming a polymer; and (3) a method of determining an amount of polymer.

(1) Method of Immobilizing Probe to Test Gene

The PALSAR methods are primarily intended to determine a test gene in a sample. In the present description, the term "immobilized probe" means one of the probes to be used which directly or indirectly binds to a test gene to be determined. A technique for immobilizing a probe to a test gene is not particularly limited, but it is preferable to bind a probe to be used in polymer formation to a test gene via an immobilization probe which has a base sequence complementary to the test gene and has the same base sequence as (or a base sequence complementary to) part or a whole of one probe to be used in polymer formation. The site in the probe to be used in polymer formation that has the same base sequence as the immobilization probe is not particularly limited, but it is preferable to select one or more regions from all regions in the probe for polymer formation. Meanwhile, an appropriate crosslinking agent may be used.

If part of one of plural kinds of probes to be used in polymer formation is designed so as to have a base sequence complementary to a test gene, the probe may be used as the immobilization probe. Meanwhile, there may be used a probe (assist probe), which additionally has both a base sequence complementary to a test gene and a base sequence complementary to a probe to be used in polymer formation. If a plurality of assist probes having base sequences different from that of a site complementary to a test gene are prepared, the assist probes have the advantage of simultaneously detecting a plurality of genes using sets of the same plurality kinds of probes.

Figure 1:
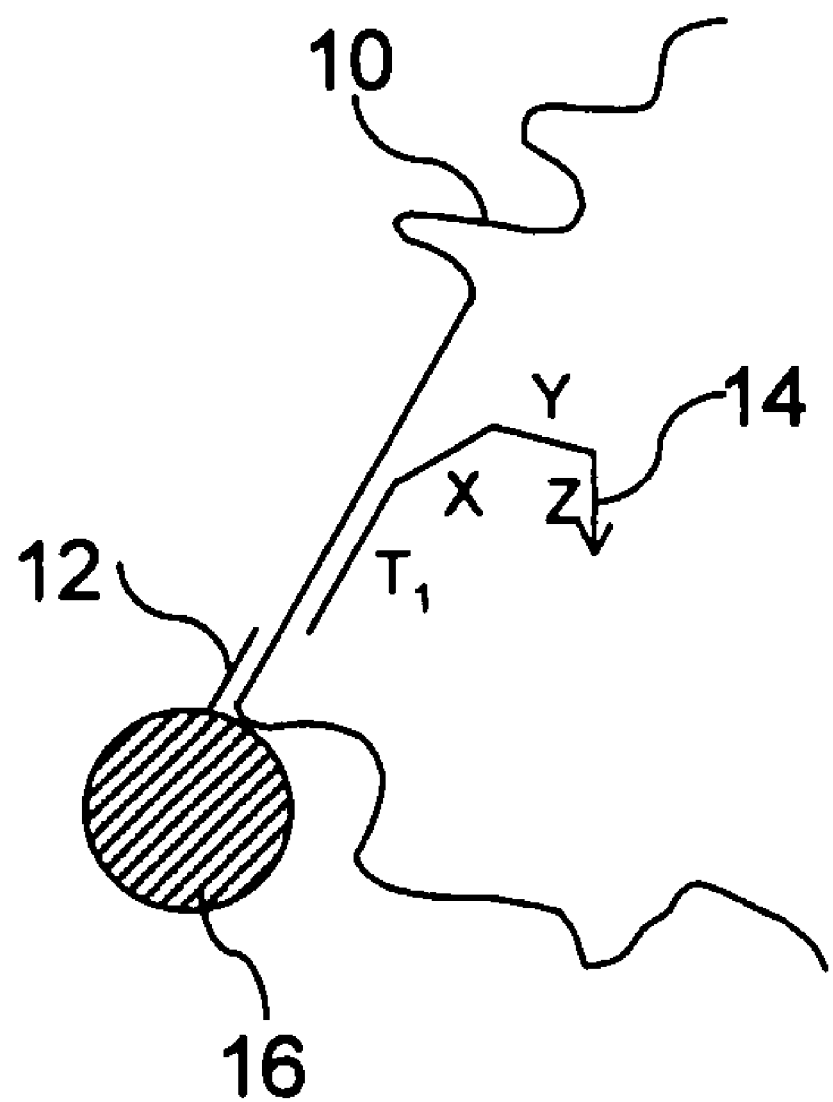
FIG. 1 is a schematic view of a probe immobilized to a test gene.

FIG. 1 is a schematic view showing an example of a method of immobilizing a probe to a test gene using an immobilization probe. A technique for immobilizing (iii) an immobilization probe 14 using (i) a test gene 10 and (ii) a capture oligonucleotide 12 shown in FIG. 1 is performed by hybridizing the following three kinds of oligonucleotides to bind (ii) the capture oligonucleotide 12 and (iii) the immobilization probe 14 via (i) the test gene 10:

(i) the test gene 10;

(ii) the capture oligonucleotide 12: an oligonucleotide complementary to a region on the test gene, preferably a region with 15 bases or more, more preferably a region with 20 bases or more; and (iii) the immobilization probe 14: a probe having a base sequence complementary to a region on the test gene and having the same base sequence as that of a first probe to be used in polymer formation (Note that the region complementary to the test gene is a region different from the region (ii), preferably a region adjacent to the region (ii) and has preferably 15 bases or more, more preferably 20 bases or more).

Note that, FIG. 1 shows an example of a method of using the below-described probe of PALSAR I, where there is used, as an immobilization probe, a probe that is represented by the following formula (11) and has a base sequence region $T_1$ complementary to a test gene and the same base sequence regions (X, Y, and Z) as a sequence of the entire of one probe to be used in polymer formation, that is, a probe that has the same base sequence as a first probe to be used in polymer formation, which is ligated to an oligonucleotide complementary to a region on a test gene, but the immobilization probe is not limited thereto.

[Chemical Formula 18]

(11)

The probes to be used for immobilization between a probe to be used in polymer formation and a test gene may be used singly or in combination of two or more. For example, as in the case of Examples 2 and 3 below, there may be used a first immobilization probe having a structure represented by the following formula (12) and a second immobilization probe having a structure represented by the following formula (13).

[Chemial Formula 19]

(12)

[Chemial Formula 20]

(13)

(In the formulas (12) and (13), $T_2$ is a region having a base sequence complementary to a test gene, A' and F' are regions each having the same base sequence as one region in a probe to be used in polymer formation, and G and G' are complementary base sequences.)

The operations may be easily performed by binding and immobilizing (ii) a capture oligonucleotide to a solid phase, preferably by immobilizing the capture oligonucleotide to a support 16 such as beads.

The hybridization may be performed in the following order. The three kinds of oligonucleotides may be hybridized simultaneously, or the items (i) and (ii) may be firstly hybridized, followed by hybridization of the item (iii). Alternatively, the items (i) and (iii) may be firstly hybridized, followed by hybridization of the item (ii). In the case where the item (ii) is immobilized, preferably, the items (i) and (iii) are firstly hybridized, followed by hybridization of the item (ii).

In some cases, the three kinds of oligonucleotides may be hybridized, followed by separately binding (ii) the capture oligonucleotide and (iii) the immobilization probe to each other, preferably binding them by a ligation reaction.

Note that, plural kinds of probes are used in polymer formation in the method (2). However, a probe to be firstly immobilized to a test gene is not particularly limited and may be freely selected from the plural kinds of probes. For the sake of convenience, a probe having the same base sequence as an immobilized probe is referred to as a first probe, while a probe having a base sequence region complementary to the first probe is referred to as a second probe.

Examples of a material of a support to determine a test gene include glass, plastic (such as polystyrene, polyamide, polyethylene, or polypropylene), and metal, and the shape of the support is not particularly limited and may be cup-shape, plate, particle, etc. The sample refers to a sample for determining the presence or absence of a test gene and includes biological fluids such as blood, serum, and cerebrospinal fluid, body tissues, microorganisms, cultured products, etc., and extracts thereof, etc.

(2) Method of Forming Polymer

A second probe is bound to an immobilized probe (having the same base sequence as a first probe), and the first and second probes are allowed to react in order, to thereby form a polymer. As the first and second probes, for example, the following probes may be used: (1) a probe of PALSAR I, (2) a probe of PALSAR II, and (3) a probe of PALSAR III.

(1) Probe of PALSAR I

The nucleotides represented by the following chemical formulas (1) and (2) are used as the first and second probes. In these formulas, X and X', Y and Y', and Z and Z' independently have base sequences complementary to each other, and the arrows means the directions of nucleotides from 5' to 3'.

[Chemical Formula 21]

(1)

$$5' \xrightarrow{\quad X \quad Y \quad Z \quad} 3'$$

[Chemical Formula 22]

(2)

$$5' \xrightarrow{\quad X' \quad Y' \quad Z' \quad} 3'$$

(2) Probe of PALSAR II

Dimer probes represented by the following chemical formulas (3) and (4) are used as the first and second probes. The dimer probes are created by hybridizing the nucleotides represented by the chemical formulas (14) and (15), respectively. In these formulas, A and A', B and B', C and C', D and D', E and E', and F and F' independently have base sequences complementary to each other, and the arrows means the directions of nucleotides from 5' to 3'.

[Chemical Formula 23]

(3)

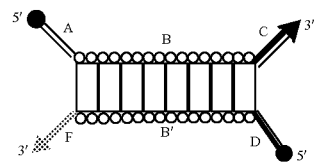

[Chemical Formula 24]

(4)

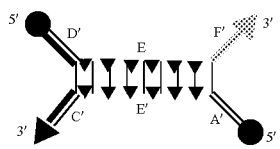

[Chemical Formula 25]

(14)

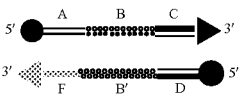

[Chemical Formula 26]

(15)

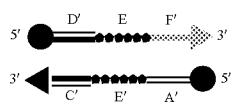

Meanwhile, a dimer probe having a structure represented by the following chemical formula (5) may be used as a dimer probe instead of the dimer probe having a structure represented by the chemical formula (4).

[Chemical Formula 27]

(5)

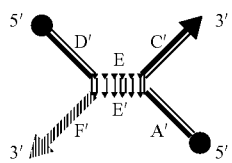

(3) Probe of PALSAR III

A dimer probe represented by the following chemical formula (6) and a crosslinking probe including two oligonucleotides represented by the following chemical formula (7) are used as the first and second probes. The dimer probe is created by hybridizing the nucleotides represented by the chemical formula (14). In these formulas, A and A', B and B', C and C', D and D', and F and F' independently have base sequences complementary to each other, and the arrows means the directions of nucleotides from 5' to 3'.

[Chemical Formula 28]

(6)

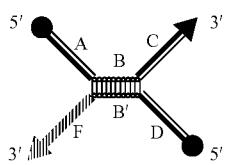

[Chemical Formula 29]

(7)

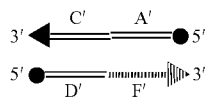

Meanwhile, two nucleotides having structures represented by the following chemical formula (8) may be used as a crosslinking probe instead of the nucleotides having structures represented by the chemical formula (7).

[Chemical Formula 30]

(8)

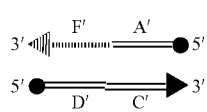

In addition, for example, an oligonucleotide having four or five complementary base sequence regions can form a polymer (Patent Document 2). Meanwhile, two kinds of dimer probes are used in the above description, but far more kinds of dimer probes may be used if the positional relationship of complementary base sequence regions is devised (Patent Document 3). As described above, the used probe may include not only the above-described probes but also other probes if the arrangement of complementary base sequence regions is devised, and the probes are within the scope of the present invention as long as they may form a self-assembly polymer.

The type of a base that composes a probe may be appropriately selected depending on a test gene, and DNA, RNA, PNA, and the like may be used. Meanwhile, the length of each complementary base sequence region of a probe is, in terms of the number of bases, at least 5 bases, preferably at least 8 bases, more preferably 10 to 100 bases, further preferably 15 to 30 bases. Meanwhile, the lengths of complementary base sequence regions of the probes are desirably the same.

FIG. 2 shows an example of a method of forming a signal probe-polymer of the present invention. FIG. 2 shows an example of using probes of PALSAR I (a first probe 22 and a second probe 24), and the numeral 20 represents a capture oligonucleotide and an immobilization probe that is immobilized to a support via a test gene. Meanwhile, FIG. 2 shows an example of a case where a capture oligonucleotide bound to biotin 30 and a support bound to avidin 32 are used to immobilize the capture oligonucleotide to the support via a bond between biotin 30 and avidin 32.

A technique for reacting probes to be used in order is performed as follows. A probe (having the same base sequence as a first probe) immobilized to a test gene bound to a support is washed, and then a second probe is allowed to react, followed by washing. Subsequently, the first and second probes can be repeatedly allowed to react in order, to thereby form a polymer. The technique is not particularly limited and includes, for example: a method shown in FIG. 2, which includes preparing a first probe reaction tank 26 containing a first probe 22, a washing tank, and a second probe reaction tank 28 containing a second probe 24, and performing a reaction by transferring a support 20 to which a test gene and an immobilization probe are immobilized in the stated order; a method described in Examples 1 to 3 below, which includes repeating addition/reaction and washing of a second probe reaction solution and addition/reaction and washing of a first probe reaction solution to a container containing the support in order; and a method including setting the support to a column and performing a reaction by passing a second probe reaction solution and a first probe reaction solution in order. According to the method of the present invention, the probe reaction solutions can be reused. In addition, in some techniques, the washing operation may be omitted.

A reaction solution to be used for a hybridization reaction may be a solution having a general composition and includes an approximately neutral buffer containing an appropriate amount of a sodium salt, a blocking agent, an additive for promoting a hybridization reaction, and the like. Those reagents to be used may be ones described in a document by Sambrook et al. (Molecular cloning 3rd ed, 2001). The temperature in polymer formation is not particularly limited as long as constituent probes can be hybridized to each other, and a polymer can be formed generally in a range of 40 to 90° C., preferably in a range of 45 to 65° C.

(3) Method of Determining Amount of Polymer

The amount of a formed polymer is determined by a method which includes binding an intercalating dye such as ethidium bromide, oligogreen, or SYBR to the polymer and detecting the polymer based on fluorescence. Meanwhile, a probe to be used may be bound in advance to a labeling substance such as a radioactive isotope, a luminescent/color-producing substance including acridium ester, a fluorescent substance, an enzyme, biotin, or digoxigenin. The labeling substance to be bound thereto is not particularly limited as long as it has no influence on polymer formation.

The determination may be performed by a method suitable for a labeling substance. That is, the method includes determination of radioactivity in the case of a radioactive isotope, determination of emitted light in the case of a luminescent substance, colorimetry in the case of a color-producing substance, determination of fluorescence in the case of a fluorescent substance, and determination of an enzymatic activity in the case of an enzyme.

In the case of labeling with biotin, digoxigenin, or the like, a labeled avidin, anti-digoxigenin antibody, etc. which specifically binds to the biotin, digoxigenin, or the like is bound thereto, and determination is performed by a method suitable for the labeling substance.

EXAMPLES

Hereinafter, the present invention will be specifically described based on examples but is not limited to the following examples without departing from the scope of the present invention.

Example 1

Determination of Cell Number of *Staphylococcus aureus* Using PALSAR I Probe (1) Preparation of Solutions
(1-1) Preparation of Lysate

*Staphylococcus aureus* was cultured in tryptic soy agar for 18 hours and then suspended in physiological saline, to thereby yield a stock culture solution. The solution was diluted with physiological saline so as to have a predetermined cell number, and the cells were lysed in accordance with a method of Birnboim et al. (H. C. Birnboim et al Nuc Acids Res 1979 7 1513-1523), to thereby yield a lysate, which was used in the following examples. To determine the cell number, a dilution series of the stock culture solution was prepared and cultured in tryptic soy agar to yield viable cells, and a given cell number was calculated from the number of the viable cells. Note that, a sample that was subjected to a similar reaction using physiological saline instead of the diluted cell solution was used as a control and represented as [(−)].

(1-2) Preparation of First Hybridization Solution

A first hybridization solution was prepared so as to have the following composition.

A solution of 12×SSC and 12.5% polyethylene glycol #20000 containing capture oligonucleotide-1 (SEQ ID NO: 1) and an immobilization probe-1 (SEQ ID NO: 2) (2.5 μmol/μL each).

The sequences of capture oligonucleotide-1 and immobilization probe-1 were designed as follows so as to capture 23s rRNA of *Staphylococcus aureus* (based on GENBANK Accession No. NC 003923.1 GI: 21281729).

The base sequence of capture oligonucleotide-1 (with biotin-labeled 3'-end) (SEQ ID NO: 1)

5'-cggaatttca cgtgctccgt ccgacgacga cgacgacgac gttttttttt ttttttttt tttttt-3'-Biotin The base sequence of immobilization probe-1 (SEQ ID NO: 2)

5' Region T₁ (gagacaacattttcgactaca) Region X (catgtctcgagtcttgcttg) Region Y (ctgctacagtgatcacc ag) Region Z (gttctcgacatagaccagtc)-3'

(1-3) Preparation of Hybridization Solution A and Hybridization Solution B

Probe-1 and digoxigeninated probe-2 having the following base sequences were separately created as a pair of probes of PALSAR I.

The base sequence of probe-1 (SEQ ID NO: 3)

5'-Region X (catgtctcgagtcttgcttg) Region Y (ctgctacagtgatcaccaag) Region Z (gttctcgacatagaccagtc)-3'

The base sequence of probe-2 (with digoxigenin-labeled 5'-end) (SEQ ID NO: 4)

5'-DIG- Region X' (caagcaagactcgagacatg) Region

Y' (cttggtgatcactgtagcag) Region Z' (gactggtctatgt cgagaac)-3'

Hybridization solution A and hybridization solution B were separately prepared so as to have the following compositions.

Hybridization Solution A:

A solution of 6×SSC, 0.3% sodium dodecyl sulfate, and 5% polyethylene glycol #20000 containing a 10 μmol/μL probe-2 (SEQ ID NO: 4).

Hybridization Solution B:

A solution of 6×SSC, 0.3% sodium dodecyl sulfate, and 5% polyethylene glycol #20000 containing a 10 pmol/μL probe-1 (SEQ ID NO: 3).

(2) Signal Amplification by PALSAR I

Lysates of *Staphylococcus aureus* (100 μL) having cell numbers (CFU/mL) of $5 \times 10^5$, $5 \times 10^4$, $5 \times 10^3$, $5 \times 10^2$, $5 \times 10^1$, and (−) were used as test samples, respectively. Each test sample and the first hybridization solution (100 μL) containing biotinylated capture oligonucleotide-1 and immobilization probe-1 was added to a test tube, followed by heating at 45° C. for 1 hour.

After the heating, 10 μL of avidinylated magnetic beads (DYNAL, Dynabeads M-280 Streptoavidin, 6 to $7 \times 10^6$ beads) were added to the test tube, followed by stirring at room temperature for 30 minutes. As a result of the above-described reaction, immobilized probes were formed as shown in FIG. 1. The stirring was performed using RKVSD manufactured by Appropriate Technical Resources, Inc. The magnetic beads were collected using a magnet to remove the solution after the reaction.

To the test tube containing the magnetic beads was added 200 μL of the hybridization solution A containing a probe-2, followed by heating at 45° C. for 5 minutes (see FIG. 2(*b*)). After that, only the magnetic beads were collected using a magnet to recover the hybridization solution A from the test tube. After that, 200 μL of the hybridization solution B containing a probe-1 was added to the test tube, followed by heating at 45° C. for 5 minutes (see FIG. 2(*c*)). The magnetic beads were collected to recover the hybridization solution B from the test tube (first time). Note that, in this example, a set of a reaction in the hybridization solution A and a reaction in the hybridization solution B was defined as one cycle of signal amplification.

To the test tube containing the magnetic beads was added the recovered hybridization solution A, followed by heating at 45° C. for 5 minutes (see FIG. 2(*d*)). After that, the magnetic beads were collected to recover the hybridization solution A from the test tube. After that, the recovered hybridization solution B was added to the test tube, followed by heating at 45° C. for 5 minutes (see FIG. 2(*e*)). The magnetic beads were collected to recover the hybridization solution B from the test tube (second time).

Subsequently, in the same way as above, the following procedures were performed up to fifth time: addition of the hybridization solution A/heating→collection of the magnetic beads/recovery of the solution→addition of the hybridization solution B/heating→collection of the magnetic beads/recovery of the solution. The magnetic beads were yielded after the procedures were performed once, twice, three times, and four times, respectively. The respective magnetic beads were collected and finally washed twice with 200 μL of washing solution A [50 mM Tris-HCl (pH 7.6), 0.3 M NaCl, 0.1% Triton X-100].

(3) Chemiluminescence Detection

After the washing, the test tube containing the magnetic beads was added with 200 μL of anti-digoxigenin Fab-POD conjugate (manufactured by Roche Diagnostics K.K.) diluted 1,000-fold with washing solution B [1% BSA, 50 mM Tris-HCl (pH 7.6), 0.3 M NaCl, 0.1% Triton X-100], followed by stirring at room temperature for 30 minutes. After that, the magnetic beads were collected to remove the solution and washed twice with 200 μL of the washing solution A. Then, 200 μL of 1-step TMB turbo ELISA (manufactured by Pierce) was added and allowed to react at room temperature for 15 minutes. The magnetic beads were collected, and 150 μL of an aliquot of the solution was recovered, followed by determination of the absorbance of the solution at 655 nm. The results are shown in FIG. 3.

Figure 3:
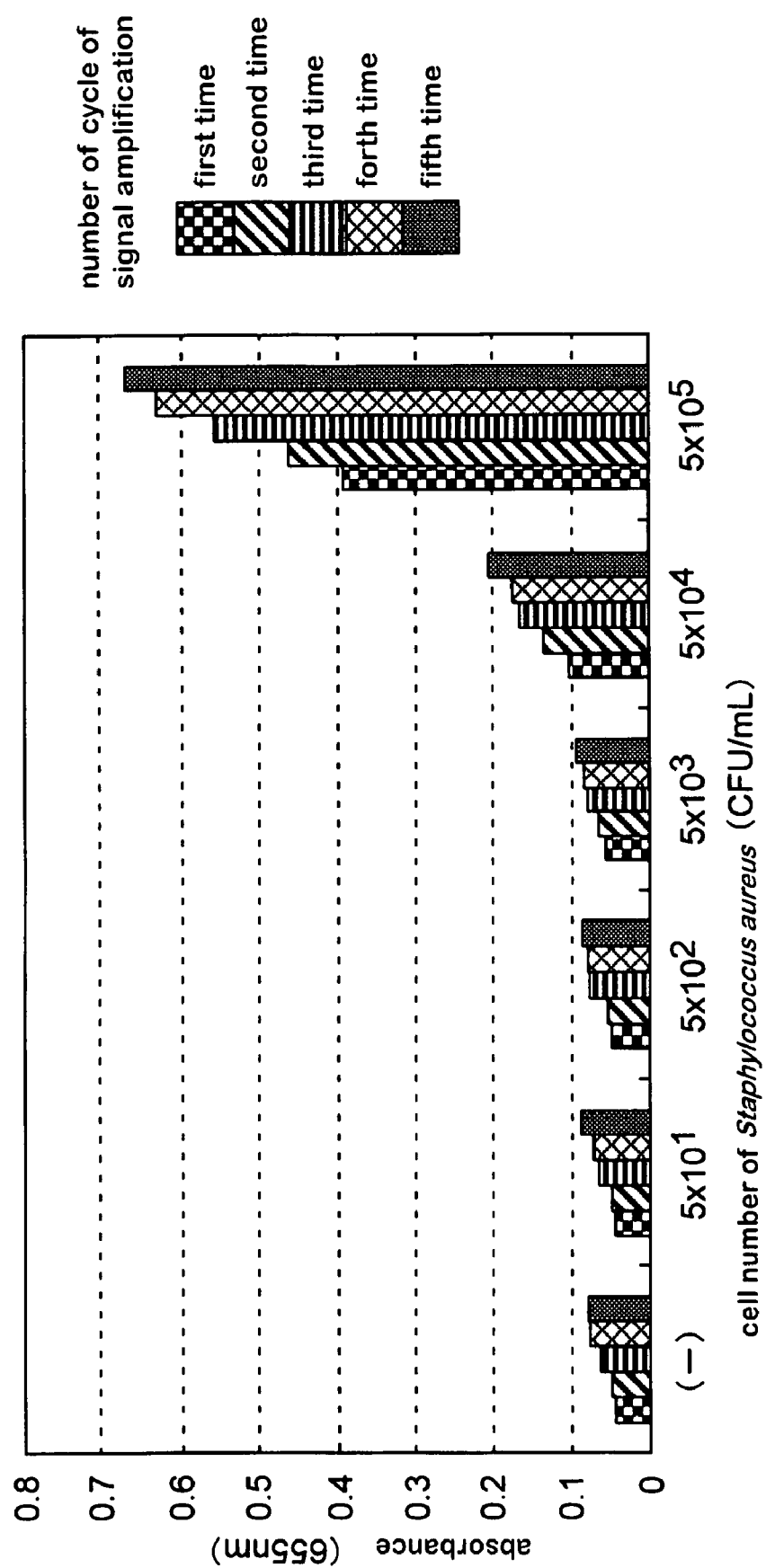
FIG. 3 is a graph showing the results of Example 1.

As a result, as shown in FIG. 3, quantitative determination could be performed for the cell numbers of *Staphylococcus aureus*. Meanwhile, the absorbance levels were found to be enhanced with increasing the number of times, thereby the effect of polymer formation being clarified.

Meanwhile, a similar experiment was performed using a radioactive isotope, biotin, a fluorescent substance, a luminescent substance, or a dye as a labeling substance instead of digoxigenin. As a result, as in the case of Example 1, quantitative determination could be performed for the cell numbers of *Staphylococcus aureus*, and the absorbance levels were found to be enhanced with increasing the number of times, thereby the effect of polymer formation being clarified.

Example 2

Detection of Synthetic HCV cRNA Using PALSAR II Probe (1) Preparation of Synthetic HCV cRNA (1-1) Preparation of Single-Stranded cDNA To a 0.2-mL microtube were added 1 μL of stored serum containing $10^{12}$ cells/μL HCV RNA, 2 μL of a 1 pmol/μL primer for cDNA synthesis, 4 μL of 2.5 mM dNTP, and 6 μL of sterilized distilled water, and the total volume was adjusted to 13 μL. The mixture was heated at 65° C. for 5 minutes, and then 4 μL of 5× First-strand buffer supplied with Superscript III (manufactured by INVITROGEN Corporation), 1 μL of 0.1 M DTT, 1 μL of RNAsin (manufactured by Promega Corporation), and 1 μL of Superscript III were added thereto, followed by heating at 50° C. for 1 hour. After that, the mixture was heated at 70° C. for 15 minutes to deactivate the enzymatic activity, to thereby prepare a cDNA solution.

Note that, the base sequence of the primer for cDNA synthesis is as follows.

5'-TGA GGT TTA GGA TTC GTG CTC-3'    (SEQ ID NO: 5)

(1-2) PCR

To 2 μL of the cDNA solution prepared above were added 40 μL of Master mixture, 0.2 μL of 5 U/μL AmpliTaq (manufactured by Applied Biosystems), and 8 μL of sterilized distilled water, and the total volume was adjusted to 50 μL. Amplification was performed under the cycle conditions shown in Table 1 below.

TABLE 1

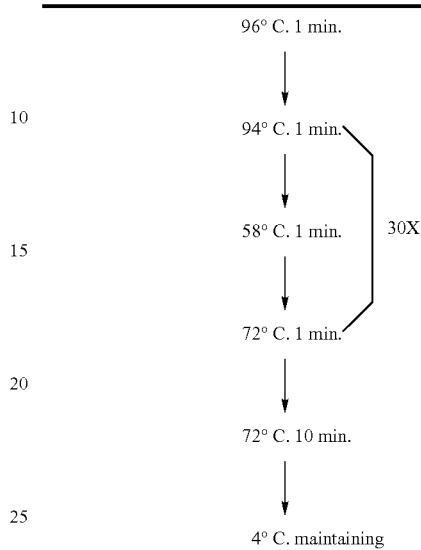

The DNA of interest amplified by the above-described PCR has about 270 base pairs.

Note that, the above-described Master mixture refers to a mixture included in Virus, Hepatitis type C virus 5' UTR, Primer set kit (Cat. No.: SP-10275) manufactured by Maxim Biotech, Inc., which was prepared by adding 250 μL of premixed primers included in the kit to 750 μL of Optimized PCR Buffer.

(1-3) Cloning

To a 1.5-mL microtube were added 2 μL of the amplified product obtained by the PCR above, 1 μL of Salt solution supplied with TOPOTA Cloning Kit for Sequencing (Invitrogen Corporation), 2 μL of sterilized distilled water, and 1 μL of TOPO cloning vector, and the solution was allowed to stand at room temperature for 5 minutes. The above-described reaction solution (2 μL) was added to *E. coli* DH5α Competent Cells (manufactured by Takara Bio Inc.), and the mixture was placed on ice for 30 minutes. The mixture was subjected to heat shock at 42° C. for 30 seconds and immediately placed on ice and allowed to stand for 2 minutes. SOC medium (250 μL) supplied with *E. coli* DH5α Competent Cells (manufactured by Takara Bio Inc.) was added thereto, followed by heating at 37° C. for 30 minutes, and 50 μL of an aliquot of the mixture was applied on an agar plate obtained by applying 50 μL of 4% Xgal (manufactured by Takara Bio Inc.) and 25 μL of IPTG (manufactured by Takara Bio Inc.) to the surface of 2×YT medium (16 g of tryptone, 10 g of yeast extract, and 5 g of sodium chloride per litter of the medium, 1.5% agar) containing 100 μg/mL ampicillin, followed by culture at 37° C. for 16 hours.

(1-4) Preparation of cRNA

A clone of interest obtained by the above-described cloning was cultured with shaking in 5 mL of 2×YT medium containing 100 μg/mL ampicillin at 37° C. for 12 hours, and QIAprep Spin Miniprep Kit (manufactured by QIAGEN) was used, to thereby yield a plasmid clone. Moreover, the sequence of an insert was determined using a DNA sequencer 3130 manufactured by Applied Biosystems. The determined sequence of HCV 5'UTR is shown below.

(SEQ ID NO: 6)
5'-AGGCCTTTCGCGACCCAACACTACTCGGCTAGCAGTCTCGCGGGGC

ACGCCCAAATCTCCAGGCATCGAGCGGGTTGATCCAAGAAAGGGCCCGGT

CGTCCTGGCAATTCCGGTGTACTCACCGGTTCCGCAGACCACTATGGCTC

TCCCGGGAGGGGGGGTCCCGGAGGCTGCACGACACTCATACTAACGCCAT

GGCTAGACGCTTTCTGCGTGAAGACAGTAGTTCCTCACAGGGGAGTGATC

TATGGTGGAGTGTCGCCCCC-3'

20 μL of a buffer supplied with an enzyme, that is, 50 U of PstI (manufactured by Takara Bio Inc.), was added to 10 μg of the resultant plasmid clone, and the total volume was adjusted to 200 μL with sterilized distilled water, followed by a reaction at 37° C. for 3 hours, to thereby yield completely linear DNA. To 1 μg of the linear DNA were added 2 μL of 10× transcription buffer supplied with T7 RNA polymerase (manufactured by Roche Diagnostics K.K.), 1 μL of 10 mM ribonucleotide mix (manufactured by Roche Diagnostics K.K.), and 1 μL of RNase inhibitor (manufactured by Roche Diagnostics K.K.), and the total volume was adjusted to 20.5 μL with sterilized distilled water, followed by a reaction at 37° C. for 2 hours. After that, 2 μL of DNase I (manufactured by Roche Diagnostics K.K.) was added thereto, and the mixture was allowed to react at 37° C. for 15 minutes. To the mixture were added 100 μL of TE (10 mM Tris-HCl, 1 mM EDTA, pH 8.0), 10 μL of 4M LiCl, and 300 μL of ethanol, and the resultant mixture was placed at −80° C. for 30 minutes. Centrifugation was performed at 4° C. and 15,000 rpm for 10 minutes, to thereby recover cRNA as a precipitate. The precipitate was washed with 500 μL of 70% ethanol and then dried, and the resultant was dissolved in 10 μL of TE (pH 8.0). The concentration was calculated based on the absorbance at 260 nm.

(2) Preparation of Solutions (2-1) Preparation of Dimers for PALSAR II

Figure 4:
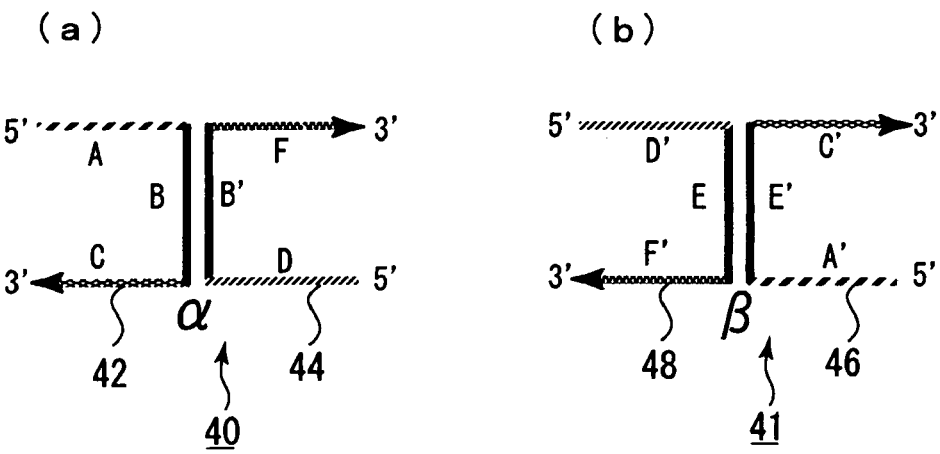
FIG. 4 is Illustrative drawings showing two sets of dimers α and β used in Example 2.

To create two sets of dimers α and β for PALSAR II [the reference numeral 40 in FIG. 4(*a*) and the reference numeral 41 in FIG. 4(*b*)], probes having the following base sequences were separately created.

The base sequence of dimer formation probe-1 (the reference numeral 42 in FIG. 4) (SEQ ID NO: 7) (with digoxigenin-labeled 5'-end)

5'-DIG- Region A (CAGTACAAGCACGATCTCTG) Region B (ATTTGCCAGGACTGCGTTTC) Region C (GACTGGTCTAGTCTGAG

AAC)-3'

The base sequence of dimer formation probe-2 (the reference numeral 44 in FIG. 4) (SEQ ID NO: 8) (with digoxigenin-labeled 5'-end)

5'-DIG- Region D (GCATAGGACTTTGTGAGCAC) Region B'

(GAAACGCAGTCCTGGCAAAT) Region F (TCAGCACTAACTTCCGT

CAC)-3'

The base sequence of dimer formation probe-3 (the reference numeral 46 in FIG. 4) (SEQ ID NO: 9) (with digoxigenin-labeled 5'-end)

5'-DIG- Region A' (CAGAGATCGTGCTTGTACTG) Region E'

(TCAGCTGCTACGAGACCATA) Region C' (GTTCTCAGACTAGACC

AGTC)-3'

The base sequence of dimer formation probe-4 (the reference numeral 48 in FIG. 4) (SEQ ID NO: 10) (with digoxigenin-labeled 5'-end)

5'-DIG- Region D' (GTGCTCACAAAGTCCTATGC) Region E (TATGGTCTCGTAGCAGCTGA) Region F' (GTGACGGAAGTTAGTG

CTGA)-3'

The dimer formation probes-1 and 2 (10 μmol each) were added to a 0.2-mL microtube, and 25×SSC was added to a final concentration of 4×SSC, followed by adjustment of the total volume to 10 μL with sterilized distilled water. The solution was heated at 98° C. for 2 minutes and then immediately heated at 57° C. for 1 hour, to thereby prepare a dimer a solution containing dimer α. Meanwhile, the same procedures were performed except that dimer formation probes-3 and 4 were used instead of the dimer formation probes-1 and 2, to thereby prepare a dimer β solution containing dimer β.

(2-2) Preparation of Hybridization Solutions A and B

A [4×SSC and 0.1% sodium dodecyl sulfate] solution containing 0.1 μL of the dimer α solution per 200 μL of the solution was prepared and used as hybridization solution A. Meanwhile, the same procedures were performed except that the dimer β solution was used instead of the dimer a solution, to thereby prepare hybridization solution B.

(2-3) Preparation of First Hybridization Solution

Capture oligonucleotide-2 was designed as follows to capture a test gene, i.e., the cRNA prepared above. Meanwhile, to immobilize the dimer a to a test gene, the following immobilization probes-2 and 3 were created.

The base sequence of the capture oligonucleotide-2 (the reference numeral 50 in FIG. 5) (SEQ ID NO: 11) (with biotin-labeled 5'-end)

5'-Biotin-ACA CTC ATA CTA ACG-3'

The base sequence of the immobilization probe-2 (the reference numeral 52 in FIG. 5) (SEQ ID NO: 12)

5'- Region A' (CAGAGATCGTGCTTGTACTG) Region G (TGC

GATAACCAATGTCAGGC) Region $T_2$ (GCTAGACGCTTTCTGCGTG

A)-3'

The base sequence of the immobilization probe-3 (the reference numeral 54 in FIG. 5) (SEQ ID NO: 13)

5'- Region G' (GCCTGACATTGGTTATCGCA) Region F' (GT

GACGGAAGTTAGTGCTGA)-3'

A first hybridization solution was prepared so as to have the following composition.

A solution of 4×SSC, 5% polyethylene glycol #20000, and 0.1% sodium dodecyl sulfate containing the capture oligonucleotide-2 and immobilization probes-2 and 3 (2.5 pmol each).

(3) Signal Amplification by PALSAR II

Figure 5:
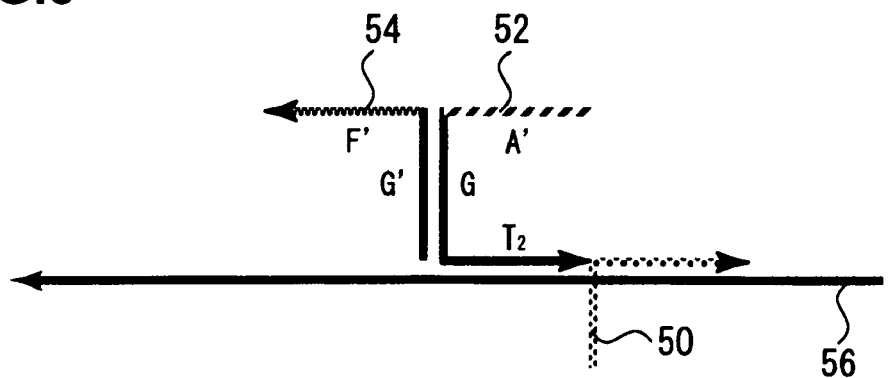
FIG. 5 is an illustrative drawing showing a first reaction in a signal amplification reaction step in Example 2.
Figure 6:
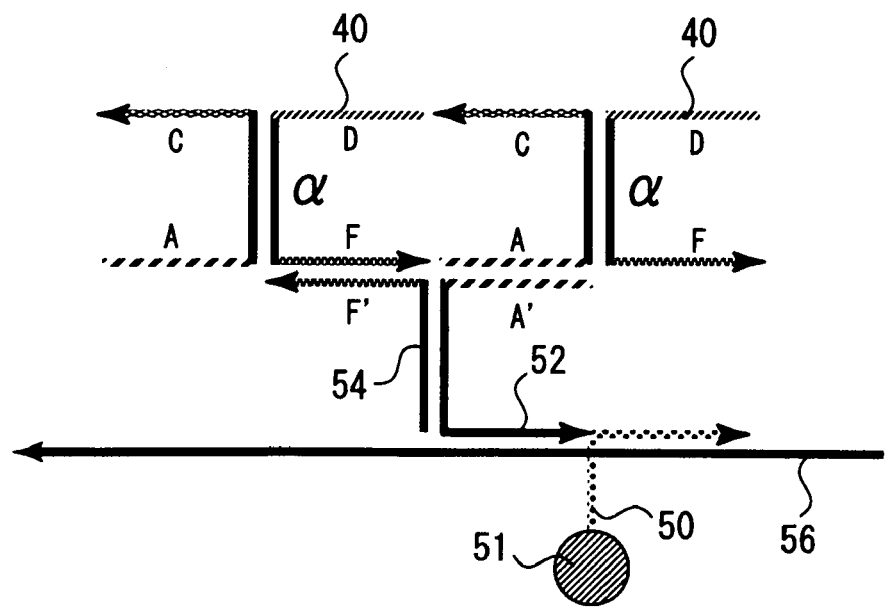
FIG. 6 is an illustrative drawing showing a second reaction in the signal amplification reaction step in Example 2.
Figure 7:
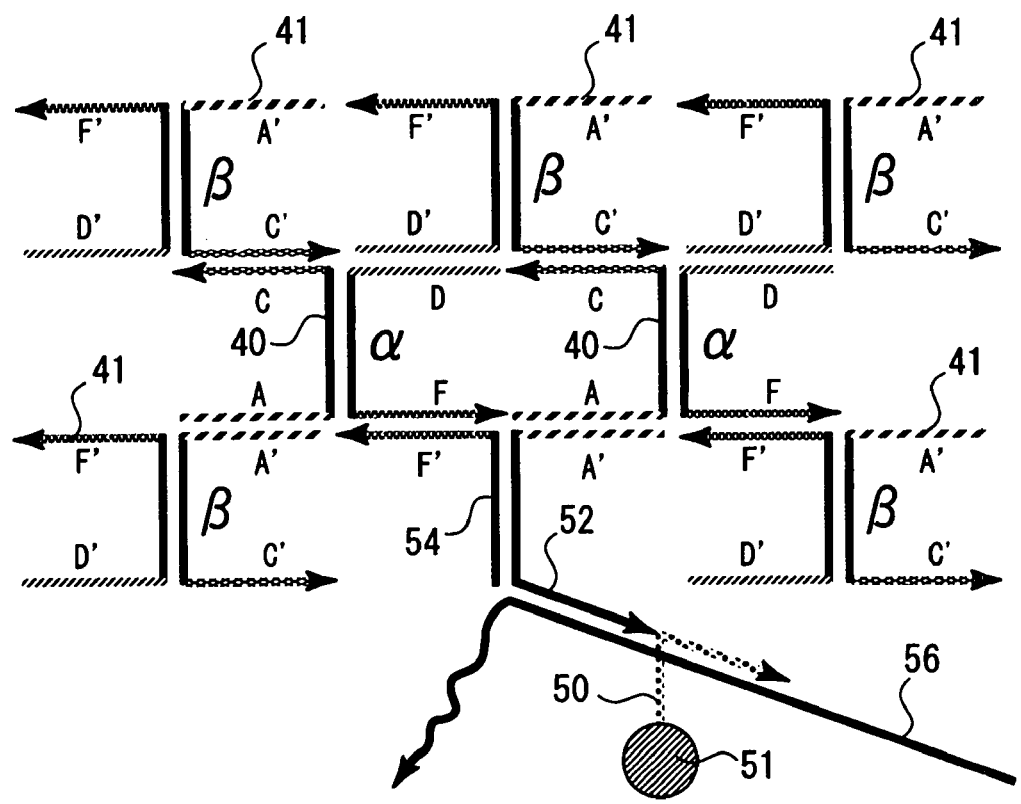
FIG. 7 is an illustrative drawing showing a third reaction in the signal amplification reaction step in Example 2.

As a sample, 100 μL of sterilized distilled water containing 8 ng of the cRNA prepared above was used. The sample and 100 μL of the first hybridization solution containing biotinylated capture oligonucleotide-2 and immobilization probes-2 and 3 were added to a test tube, followed by heating at 45° C. for 1 hour (first reaction). FIGS. 5 to 7 are schematic illustrations showing steps of signal amplification reactions in Example 2, and FIG. 5 is a schematic illustration showing the first reaction. Note that, in FIG. 5, the reference numeral 56 represents a test gene, HCV cRNA.

After the heating, 10 μL of avidinylated magnetic beads (DYNAL, Dynabeads M-280 Streptoavidin, 6 to 7×10$^6$ beads) were added to the test tube, followed by stirring at room temperature for 30 minutes. The stirring was performed using RKVSD manufactured by Appropriate Technical Resources, Inc. The magnetic beads were collected using a magnet to remove the solution after the reaction.

To the test tube containing the magnetic beads was added 200 μL of the hybridization solution A containing dimer α, followed by heating at 45° C. for 10 minutes (second reaction). FIG. 6 is a schematic illustration showing the second reaction. Note that, in FIG. 6, the reference numeral 51 represents a support, i.e., one of the magnetic beads. After that, only the magnetic beads were collected using a magnet to recover the hybridization solution A from the test tube. After that, 200 μL of the hybridization solution B containing dimer β was added to the test tube, followed by heating at 45° C. for 10 minutes (third reaction). FIG. 7 is a schematic illustration showing the third reaction. The magnetic beads were collected to recover the hybridization solution B from the test tube (first time). Note that, in this example, a set of a reaction in the hybridization solution A and a reaction in the hybridization solution B was defined as one cycle of signal amplification.

The recovered hybridization solution A was added to the test tube containing the magnetic beads, followed by heating at 45° C. for 10 minutes. After that, the magnetic beads were collected to recover the hybridization solution A from the test tube. After that, the recovered hybridization solution B was added to the test tube, followed by heating at 45° C. for 10 minutes. The magnetic beads were collected to recover the hybridization solution B (second time).

Subsequently, in the same way as above, the following procedures were performed: addition of the hybridization solution A/heating→collection of the magnetic beads/recovery of the solution→addition of the hybridization solution B/heating→collection of the magnetic beads/recovery of the solution (third time). The magnetic beads were yielded after the procedures were performed once and twice, respectively. The respective magnetic beads were collected and finally washed twice with 200 μL of washing solution A [50 mM Tris-HCl (pH 7.6), 0.3 M NaCl, 0.1% Triton X-100].

(4) Chemiluminescence Detection

After the washing, the magnetic beads were collected, and 200 μL of anti-digoxigenin Fab-POD conjugate (manufactured by Roche Diagnostics K.K.) diluted 1,000-fold with washing solution B [1% BSA, 50 mM Tris-HCl (pH 7.6), 0.3 M NaCl, 0.1% Triton X-100] was added, followed by stirring at room temperature for 30 minutes. The stirring was performed using RKVSD manufactured by Appropriate Technical Resources, Inc. After that, the magnetic beads were collected to remove the solution and washed twice with 200 μL of the washing solution A. Then, 200 μL of 1-step TMB turbo ELISA (manufactured by Pierce) was added and allowed to react at room temperature for 5 minutes, and 40 μL of 5N sulfuric acid was added to terminate the reaction. The magnetic beads were collected, and 150 μL of an aliquot of the solution was recovered, followed by determination of the absorbance of the solution at 450 nm. The results are shown in FIG. 8.

Figure 8:
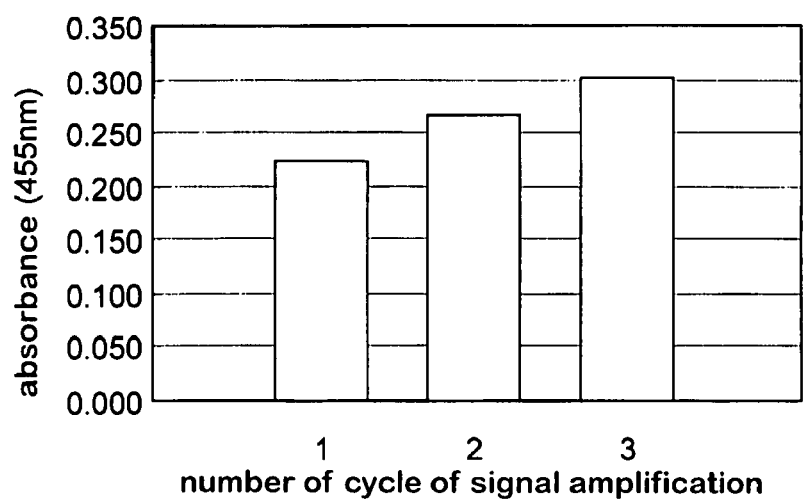
FIG. 8 is a graph showing the results of Example 2.

As a result, as shown in FIG. 8, the absorbance levels were found to be enhanced with increasing the number of times, thereby the effect of polymer formation being clarified.

Meanwhile, a similar experiment was performed using a radioactive isotope, biotin, a fluorescent substance, a luminescent substance, or a dye as a labeling substance instead of digoxigenin. As a result, the absorbance levels were found to be enhanced with increasing the number of times, thereby the effect of polymer formation being clarified.

Example 3

Detection of Synthetic HCV cRNA Using PALSAR III Probe

Figure 9:
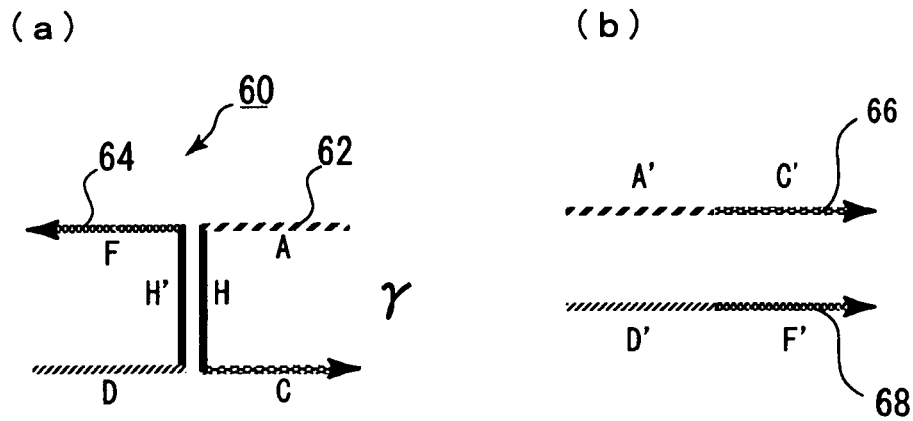
FIG. 9 is Illustrative drawings showing one set of dimer γ and one set of crosslinking probes used in Example 3.

(1) Preparation of Solutions (1-1) Preparation of Dimers and Crosslinking Probes for PALSAR III To create a set of dimer γ [the reference numeral 60 in FIG. 9(*a*)] and a set of crosslinking probes [FIG. 9(*b*)] for PALSAR III, probes having the following base sequences were separately created.

The base sequence of dimer formation probe-5 (the reference numeral 62 in FIG. 9) (SEQ ID NO: 14) (with digoxigenin-labeled 5'-end)

5'-DIG- Region A (CAGTACAAGCACGATCTCTG) Region H (GATGGTGTTCACTGTAGCAG) Region C (GACTGGTCTAGTCTGAG AAC)-3'

The base sequence of dimer formation probe-6 (the reference numeral 64 in FIG. 9) (SEQ ID NO: 15) (with digoxigenin-labeled 5'-end)

5'-DIG- Region D (GCATAGGACTTTGTGAGCAC) Region H' (CTGCTACAGTGAACACCATC) Region F (TCAGCACTAACTTCCGT CAC)-3'

The base sequence of crosslinking probe-1 (the reference numeral 66 in FIG. 9) (SEQ ID NO: 16)

5'- Region A' (CAGAGATCGTGCTTGTACTG) Region C' (GT TCTCAGACTAGACCAGTC)-3'

The base sequence of crosslinking probe-2 (the reference numeral 68 in FIG. 9) (SEQ ID NO: 17)

5'- Region D' (GTGCTCACAAAGTCCTATGC) Region F' (GT GACGGAAGTTAGTGCTGA)-3'

The dimer formation probes-5 and 6 (10 pmol each) were added to a 0.2-mL microtube, and 25×SSC was added to a final concentration of 4×SSC, followed by adjustment of the total volume to 10 μL with sterilized distilled water. The solution was heated at 98° C. for 2 minutes and then immediately heated at 57° C. for 1 hour, to thereby prepare a dimer γ solution containing dimer γ.

(1-2) Preparation of Hybridization Solutions A and B

A [4×SSC and 0.1% sodium dodecyl sulfate] solution containing 5 μL of the dimer γ solution per 200 μL of the solution was prepared and used as hybridization solution A. Meanwhile, hybridization solution B was prepared so as to have the following composition.

A solution of 4×SSC and 0.1% sodium dodecyl sulfate containing 5 pmol of the crosslinking probes-1 and 2.

(1-3) Preparation of First Hybridization Solution

A solution having the following composition was used as a first hybridization solution.

A solution of 4×SSC, 5% polyethylene glycol #20000, and 0.1% sodium dodecyl sulfate containing biotinylated capture oligonucleotide-2 (SEQ ID NO: 11), immobilization probe-2 (SEQ ID NO: 12), and immobilization probe-4 (SEQ ID NO: 18) (2.5 pmol each).

Note that, the capture oligonucleotide-2 and immobilization probe-2 is the same as those used in Example 2, and the immobilization probe-4 (the reference numeral 70 in FIG. 10) has the following base sequence.

(SEQ ID NO: 18)
5'- Region G' (GCCTGACATTGGTTATCGCA) Region C' (GTTCTCAGACTAGACCAGTC)-3'

(2) Signal Amplification by PALSAR III

Figure 10:
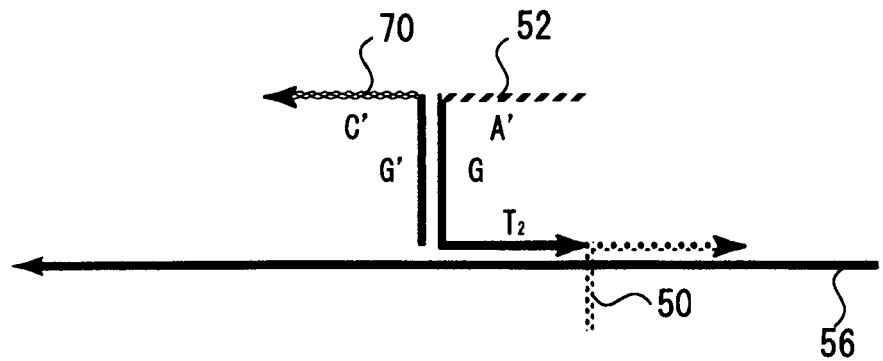
FIG. 10 is an illustrative drawing showing a first reaction in a signal amplification reaction step in Example 3.

As a sample, 100 μL of sterilized distilled water containing 10 ng of the cRNA prepared in the same manner as in Example 2 was used. The sample and 100 μL of the first hybridization solution containing capture oligonucleotide-2 and immobilization probes-2 and 4 were added to a test tube, followed by heating at 45° C. for 1 hour (first reaction). FIGS. 10 to 13 are schematic illustrations showing steps of signal amplification reactions in Example 3, and FIG. 10 is a schematic illustration showing the first reaction.

After the heating, 10 μL of avidinylated magnetic beads (DYNAL, Dynabeads M-280 Streptoavidin, 6 to 7×10$^6$ beads) were added to the test tube, followed by stirring at room temperature for 30 minutes. The stirring was performed using RKVSD manufactured by Appropriate Technical Resources, Inc. The magnetic beads were collected using a magnet to remove the solution after the reaction.

Figure 11:
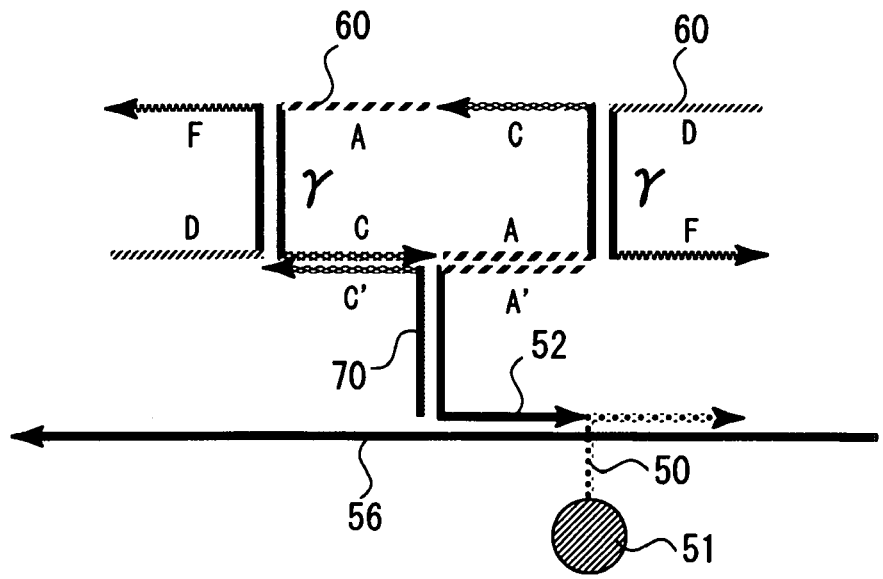
FIG. 11 is an illustrative drawing showing a second reaction in the signal amplification reaction step in Example 3.
Figure 12:
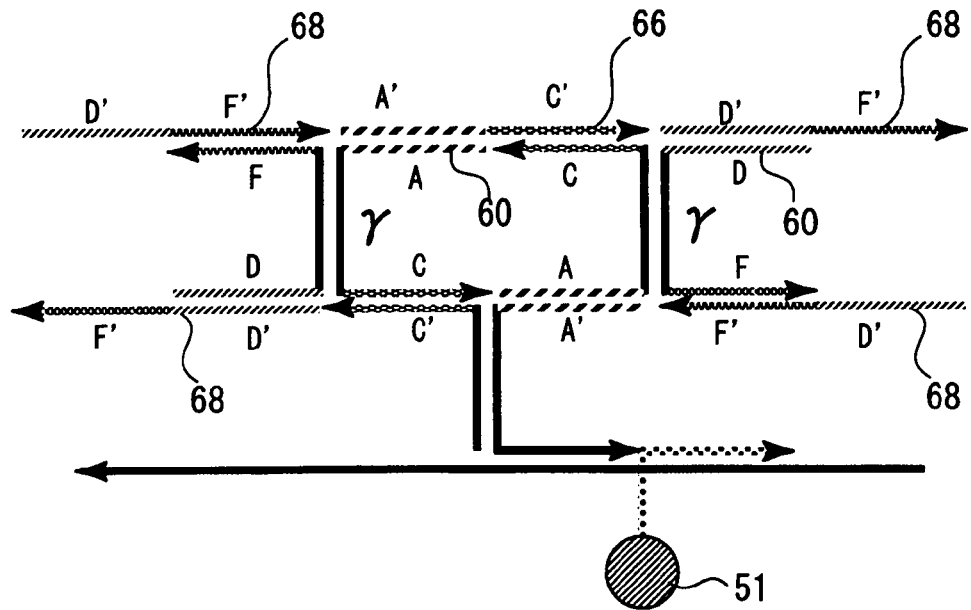
FIG. 12 is an illustrative drawing showing a third reaction in the signal amplification reaction step in Example 3.

To the test tube containing the magnetic beads was added 200 μL of the hybridization solution A containing dimer γ, followed by heating at 45° C. for 10 minutes (second reaction). FIG. 11 is a schematic illustration showing the second reaction. After that, only the magnetic beads were collected using a magnet to recover the hybridization solution A from the test tube. After that, 200 μL of the hybridization solution B containing the crosslinking probes-1 and 2 was added to the test tube, followed by heating at 45° C. for 10 minutes (third reaction). FIG. 12 is a schematic illustration showing the third reaction. The magnetic beads were collected to recover the hybridization solution B from the test tube (first time). Note that, in this example, a set of a reaction in the hybridization solution A and a reaction in the hybridization solution B was defined as one cycle of signal amplification.

Figure 13:
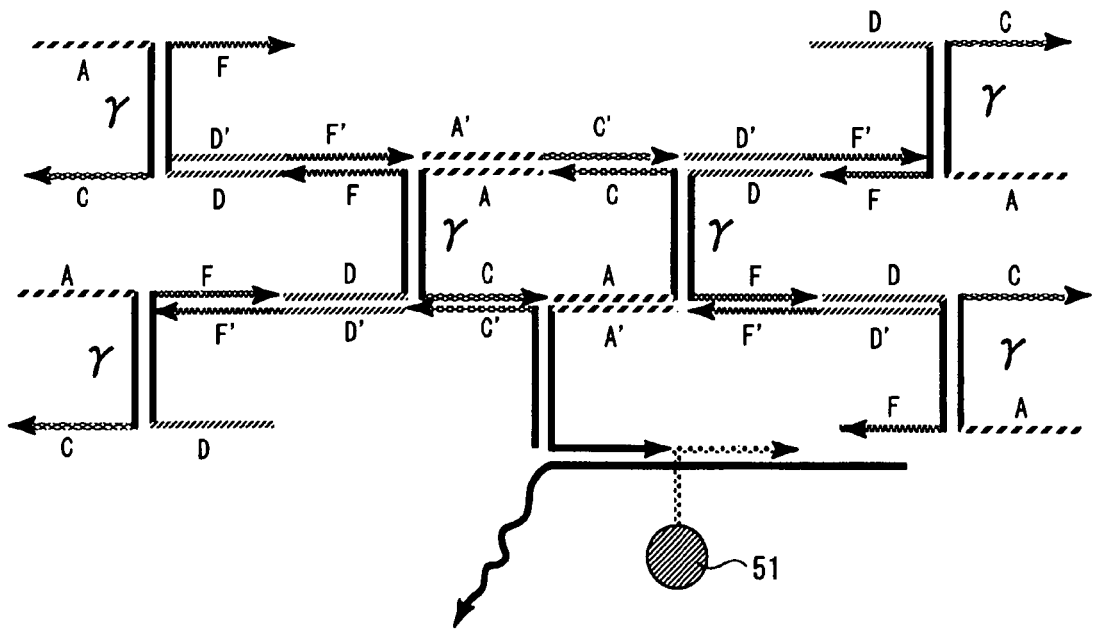
FIG. 13 is an illustrative drawing showing a fourth reaction in the signal amplification reaction step in Example 3.

The recovered hybridization solution A was added to the test tube containing the magnetic beads, followed by heating at 45° C. for 10 minutes (fourth reaction). FIG. 13 is a schematic illustration showing the fourth reaction. After that, the magnetic beads were collected to recover the hybridization solution A from the test tube. After that, the recovered hybridization solution B was added to the test tube, followed by heating at 45° C. for 10 minutes. The magnetic beads were collected to recover the hybridization solution B (second time).

Subsequently, in the same way as above, the following procedures were performed up to fifth time: addition of the hybridization solution A/heating→collection of the magnetic beads/recovery of the solution→addition of the hybridization solution B/heating→collection of the magnetic beads/recovery of the solution. The magnetic beads were yielded after the procedures were performed once and three times, respectively, and finally washed twice with 200 μL of washing solution A [50 mM Tris-HCl (pH 7.6), 0.3 M NaCl, 0.1% Triton X-100].

(3) Chemiluminescence Detection

After the washing, the magnetic beads were collected, and 200 μL of anti-digoxigenin Fab-POD conjugate (manufactured by Roche Diagnostics K.K.) diluted 1,000-fold with washing solution B [1% BSA, 50 mM Tris-HCl (pH 7.6), 0.3 M NaCl, 0.1% Triton X-100], followed by stirring at room temperature for 30 minutes. The stirring was performed using RKVSD manufactured by Appropriate Technical Resources, Inc. After that, the magnetic beads were collected to remove the solution and washed twice with 200 μL of the washing solution A. Then, 200 μL of 1-step TMB turbo ELISA (manufactured by Pierce) was added and allowed to react at room temperature for 5 minutes, and 40 μL of 5N sulfuric acid was added to terminate the reaction. The magnetic beads were collected, and 150 μL of an aliquot of the solution was recovered, followed by determination of the absorbance of the solution at 455 nm. The results are shown in FIG. 14.

Figure 14:
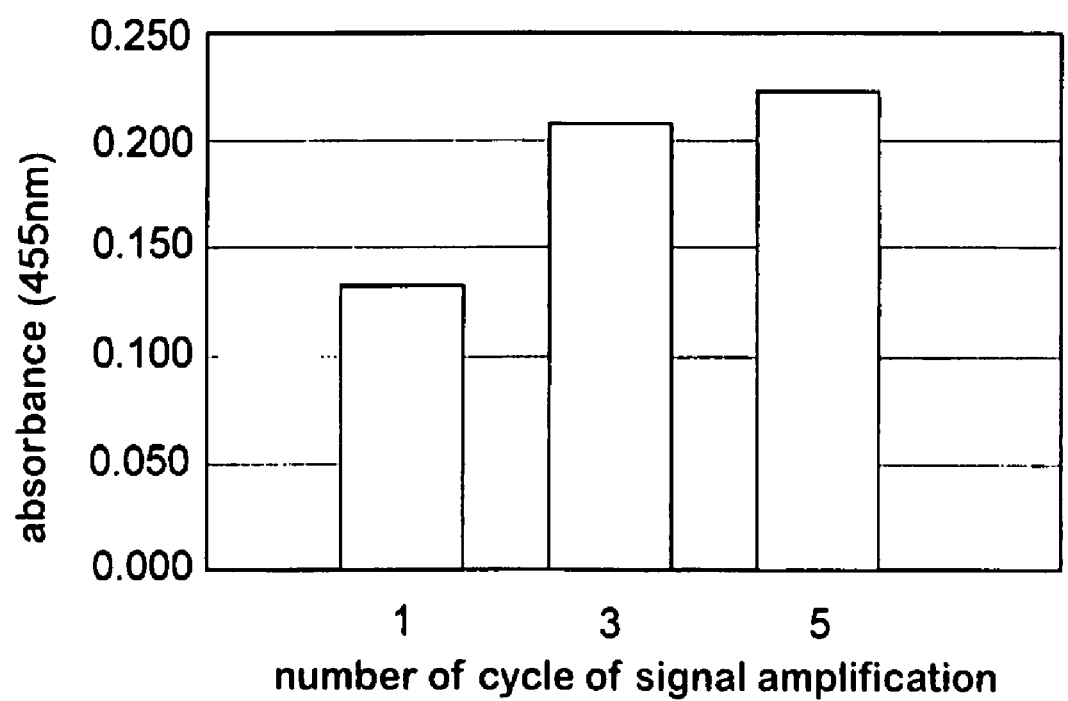
FIG. 14 is a graph showing the results of Example 3.

As a result, as shown in FIG. 14, the absorbance levels were found to be enhanced with increasing the number of times, thereby the effect of polymer formation being clarified.

Meanwhile, a similar experiment was performed using a radioactive isotope, biotin, a fluorescent substance, a luminescent substance, or a dye as a labeling substance instead of digoxigenin. As a result, the absorbance levels were found to be enhanced with increasing the number of times, thereby the effect of polymer formation being clarified.

INDUSTRIAL APPLICABILITY

The present invention has achieved suppression of a non-specific reaction and improvement in detection sensitivity in the PALSAR method. This has allowed detection of a specific gene.

The invention claimed is:

1. A method of forming a signal probe-polymer, comprising: immobilizing an immobilization probe to a test gene and then reacting plural kinds of probes to form the polymer, wherein the plural kinds of probes have base sequence regions complementary to each other and have abilities to complementarily bind to each other, wherein the polymer is formed by reacting the plural kinds of probes by contacting each kind of probe of the plural kinds of probes one by one in order and wherein after each probe of the plural kinds of probes is reacted, excess robe is removed prior to reacting another probe of the plural kinds of probe.

2. A method according to claim 1, wherein the plural kinds of probes are a probe-1 having a structure of the following chemical formula (1) including three complementary base sequence regions X, Y, and Z and a probe-2 having a structure of the following chemical formula (2) including three complementary base sequence regions X', Y', and Z', and the polymer is formed by reacting the probe-1 and the probe-2 one by one in order:

[Chemical Formula 1]

(1)

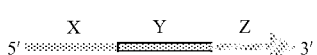

[Chemical Formula 2]

(2)

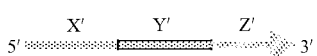

(in the formulas (1) and (2), X and X', Y and Y', and Z and Z' independently have base sequences complementary to each other).

3. A method according to claim 1, wherein the plural kinds of probes are a dimer probe-1 having a structure of the following chemical formula (3) and a dimer probe-2 having a structure of the following chemical formula (4) or (5), and the polymer is formed by reacting the dimer probe-1 and the dimer probe-2 one by one in order:

[Chemical Formula 3]

(3)

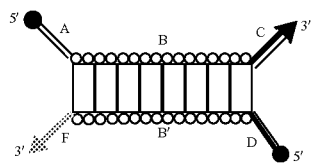

[Chemical Formula 4]

(4)

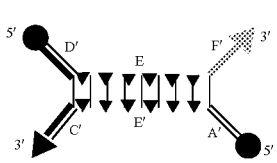

[Chemical Formula 5]

(5)

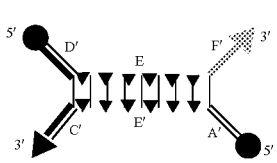

(in the formulas (3) to (5), A and A', B and B', C and C', D and D', E and E', and F and F' independently have base sequences complementary to each other).

4. A method according to claim 1, wherein the plural kinds of probes are a dimer probe-3 having a structure of the following chemical formula (6) and two crosslinking probes having structures of the following chemical formula (7) or (8), and the polymer is formed by reacting the dimer probe-3 and the crosslinking probes one by one in order:

[Chemical Formula 6]

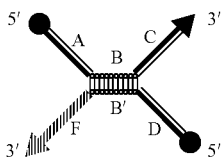

(6)

[Chemical Formula 7]

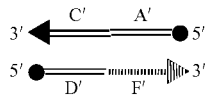

(7)

[Chemical Formula 8]

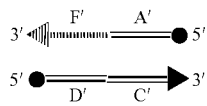

(8)

(in the formulas (6) to (8), A and A', B and B', C and C', D and D', and F and F' independently have base sequences complementary to each other).

5. A method according to claim 1, wherein the probes to be used for forming the polymer are labeled with a labeling substance.

6. A method according to claim 5, wherein the labeling substance is a radioactive isotope, biotin, digoxigenin, a fluorescent substance, a luminescent substance, or a dye.

7. A method according to claim 1, wherein the polymer is formed by immobilizing an immobilization probe to the test gene and then reacting the plural kinds of probes with the immobilized probe one by one in order, wherein the immobilization probe has the same base sequence as part or a whole of one of the probes to be used for forming the polymer and has a base sequence complementary to the test gene.

8. A method of determining a test gene, comprising: forming a polymer by a method according to any one of claims 1 to 7; and determining the test gene by determining the amount of the formed polymer.

\* \* \* \* \*

SEQUENCE LISTING

<160> NUMBER OF SEQ ID NOS: 18

<210> SEQ ID NO 1
<211> LENGTH: 66
<212> TYPE: DNA

```
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (66)..(66)
<223> OTHER INFORMATION: biotin attached at the 3' end

<400> SEQUENCE: 1
cggaatttca cgtgctccgt ccgacgacga cgacgacgac gtttttttt tttttttt        60 tttttt                                                                66

<210> SEQ ID NO 2
<211> LENGTH: 81
<212> TYPE: DNA
<213> ORGANISM: Artificial
<220> FEATURE:
<223> OTHER INFORMATION: Description of Artificial Sequence; Synthetic

<400> SEQUENCE: 2
gagacaacat tttcgactac acatgtctcg agtcttgctt gctgctacag tgatcaccaa     60
ggttctcgac atagaccagt c                                               81

<210> SEQ ID NO 3
<211> LENGTH: 60
<212> TYPE: DNA
<213> ORGANISM: Artificial
<220> FEATURE:
<223> OTHER INFORMATION: Description of Artificial Sequence; Synthetic

<400> SEQUENCE: 3
catgtctcga gtcttgcttg ctgctacagt gatcaccaag gttctcgaca tagaccagtc     60

<210> SEQ ID NO 4
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5' end

<400> SEQUENCE: 4
caagcaagac tcgagacatg cttggtgatc actgtagcag gactggtcta tgtcgagaac     60

<210> SEQ ID NO 5
<211> LENGTH: 21
<212> TYPE: DNA
<213> ORGANISM: Artificial
<220> FEATURE:
<223> OTHER INFORMATION: Description of Artificial Sequence; Synthetic

<400> SEQUENCE: 5
tgaggtttag gattcgtgct c                                               21

<210> SEQ ID NO 6
<211> LENGTH: 267
<212> TYPE: DNA
<213> ORGANISM: Hepatitis C virus

<400> SEQUENCE: 6
aggcctttcg cgacccaaca ctactcggct agcagtctcg cgggggcacg cccaaatctc     60
caggcatcga gcgggttgat ccaagaaagg gcccggtcgt cctggcaatt ccggtgtact    120
```

```
caccggttcc gcagaccact atggctctcc cgggaggggg ggtcccggag gctgcacgac      180
actcatacta acgccatggc tagacgcttt ctgcgtgaag acagtagttc ctcacagggg      240
agtgatctat ggtggagtgt cgccccc                                          267

<210> SEQ ID NO 7
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5' end

<400> SEQUENCE: 7
cagtacaagc acgatctctg atttgccagg actgcgtttc gactggtcta gtctgagaac      60

<210> SEQ ID NO 8
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5' end

<400> SEQUENCE: 8
gcataggact ttgtgagcac gaaacgcagt cctggcaaat tcagcactaa cttccgtcac      60

<210> SEQ ID NO 9
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5' end

<400> SEQUENCE: 9
cagagatcgt gcttgtactg tcagctgcta cgagaccata gttctcagac tagaccagtc      60

<210> SEQ ID NO 10
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5' end

<400> SEQUENCE: 10
gtgctcacaa agtcctatgc tatggtctcg tagcagctga gtgacggaag ttagtgctga      60

<210> SEQ ID NO 11
<211> LENGTH: 15
<212> TYPE: DNA
<213> ORGANISM: Artificial
<220> FEATURE:
<223> OTHER INFORMATION: Description of Artificial Sequence; Synthetic
<220> FEATURE:
```

```
<221> NAME/KEY: misc_feature
<222> LOCATION: (1)..(1)
<223> OTHER INFORMATION: biotin attached at the 5' end

<400> SEQUENCE: 11
acactcatac taacg                                                        15

<210> SEQ ID NO 12
<211> LENGTH: 60
<212> TYPE: DNA
<213> ORGANISM: Artificial
<220> FEATURE:
<223> OTHER INFORMATION: Description of Artificial Sequence; Synthetic

<400> SEQUENCE: 12
cagagatcgt gcttgtactg tgcgataacc aatgtcaggc gctagacgct ttctgcgtga      60

<210> SEQ ID NO 13
<211> LENGTH: 40
<212> TYPE: DNA
<213> ORGANISM: Artificial
<220> FEATURE:
<223> OTHER INFORMATION: Description of Artificial Sequence; Synthetic

<400> SEQUENCE: 13
gcctgacatt ggttatcgca gtgacggaag ttagtgctga                            40

<210> SEQ ID NO 14
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5' end

<400> SEQUENCE: 14
cagtacaagc acgatctctg gatggtgttc actgtagcag gactggtcta gtctgagaac      60

<210> SEQ ID NO 15
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5' end

<400> SEQUENCE: 15
gcataggact ttgtgagcac ctgctacagt gaacaccatc tcagcactaa cttccgtcac      60

<210> SEQ ID NO 16
<211> LENGTH: 40
<212> TYPE: DNA
<213> ORGANISM: Artificial
<220> FEATURE:
<223> OTHER INFORMATION: Description of Artificial Sequence; Synthetic

<400> SEQUENCE: 16
cagagatcgt gcttgtactg gttctcagac tagaccagtc                            40

<210> SEQ ID NO 17
<211> LENGTH: 40
```

-continued

```
<212> TYPE: DNA
<213> ORGANISM: Artificial
<220> FEATURE:
<223> OTHER INFORMATION: Description of Artificial Sequence; Synthetic

<400> SEQUENCE: 17
gtgctcacaa agtcctatgc gtgacggaag ttagtgctga                              40

<210> SEQ ID NO 18
<211> LENGTH: 40
<212> TYPE: DNA
<213> ORGANISM: Artificial
<220> FEATURE:
<223> OTHER INFORMATION: Description of Artificial Sequence; Synthetic

<400> SEQUENCE: 18
gcctgacatt ggttatcgca gttctcagac tagaccagtc                              40
```